United States Patent [19]
Mendizabal

[11] Patent Number: 5,861,141
[45] Date of Patent: *Jan. 19, 1999

[54] PHARMACEUTICAL FORMULATIONS OF CEFACLOR

[75] Inventor: Flavia Arce Mendizabal, Madrid, Spain

[73] Assignee: Lilly S.A., Madrid, Spain

[*] Notice: This patent issued on a continued prosecution application filed under 37 CFR 1.53(d), and is subject to the twenty year patent term provisions of 35 U.S.C. 154(a)(2).

[21] Appl. No.: 542,853

[22] Filed: Oct. 13, 1995

[30] Foreign Application Priority Data

Dec. 13, 1994 [ES] Spain ..................................... 9402530

[51] Int. Cl.$^6$ ................. A61K 9/20; A61K 9/46; A61K 31/545
[52] U.S. Cl. ................. 424/44; 424/464; 424/465; 424/466; 514/960; 514/200
[58] Field of Search .............. 424/44, 464, 465, 424/466; 514/960

[56] References Cited

U.S. PATENT DOCUMENTS

| | | | |
|---|---|---|---|
| 3,931,404 | 1/1976 | Fulberth et al. | 424/246 |
| 4,143,129 | 3/1979 | Marsden | 424/80 |
| 4,950,484 | 8/1990 | Olthoff et al. | 424/464 |
| 5,445,827 | 8/1995 | Fritsch et al. | 424/466 |
| 5,503,846 | 4/1996 | Wehling et al. | 424/466 |
| 5,506,248 | 4/1996 | Nikfar et al. | 514/374 |
| 5,514,383 | 5/1996 | Laly et al. . | |
| 5,556,639 | 9/1996 | Fielden | 424/480 |
| 5,587,172 | 12/1996 | Cherukuri et al. | 424/401 |
| 5,587,180 | 12/1996 | Allen et al. | 424/499 |
| 5,595,761 | 1/1997 | Allen et al. | 424/484 |
| 5,605,889 | 2/1997 | Curatolo et al. | 514/29 |
| 5,616,344 | 4/1997 | Battist et al. | 424/486 |
| 5,622,719 | 4/1997 | Myers et al. | 424/486 |

FOREIGN PATENT DOCUMENTS

| | | |
|---|---|---|
| 0049061 A1 | 4/1982 | European Pat. Off. . |
| 0181650 A1 | 5/1986 | European Pat. Off. . |
| 0487774 A1 | 6/1992 | European Pat. Off. . |
| 0547646 A3 | 6/1993 | European Pat. Off. . |
| 2 066 662 | 7/1981 | United Kingdom . |
| WO 91/16893 | 11/1991 | WIPO . |
| WO 92/08463 | 5/1992 | WIPO . |
| WO 92/19227 | 11/1992 | WIPO . |
| WO 93/21923 | 11/1993 | WIPO . |

*Primary Examiner*—Shep K. Rose
*Attorney, Agent, or Firm*—Arlene K. Musser; Janet T. McClain

[57] ABSTRACT

Pharmaceutical formulations of cefaclor, suitable for the direct-compression manufacture of dispersible tablets, containing the antibiotic cefaclor in an amount between 35% and 50% by weight of the total weight of the formulation, along with suitable excipients and coadjuvants selected from disintegrators, diluents, lubricants, antiadherents, sweeteners, fragrances and, optionally, flavorings, opacifiers and colorants. Said formulations are suitable for the manufacture of dispersible tablets which disintegrate in less than three minutes in water at 19°–21° C., and are suitable for the treatment of infections caused by bacteria strains sensitive to cefaclor.

22 Claims, No Drawings

PHARMACEUTICAL FORMULATIONS OF CEFACLOR

FIELD OF THE INVENTION

This invention refers to pharmaceutical formulations containing cefaclor suitable for the manufacture of solid pharmaceutical forms for oral administration. In particular, the invention refers to pharmaceutical formulations and dispersible tablets containing cefaclor, and their manufacturing process.

BACKGROUND OF THE INVENTION

Cefaclor or 3-chloro-7-D-(phenylglycinamide)-3-cephem-4-carboxylic acid is a semi-synthetic cephalosporinic antibiotic described for example in U.S. Pat. No. 3,925,372 and German Patent No. DE 2,408,698 (Eli Lilly & Co.). Its bactericide action is based on its capacity to inhibit cell wall synthesis. Cefaclor is indicated for treatment of infections caused by sensitive strains of numerous organisms, particularly Streptococcus and Staphylococcus.

Pharmaceutical forms currently available for administration of cefaclor include capsules, retard tablets and suspensions, both in phial and sachet form.

There are a number of limitations and drawbacks to the use of capsules affecting the following:

their administration to the patient, which may be limited because some may have problems in swallowing them, particularly children and the elderly who may even be unable to do so; and the fact that they permit only a single dosage.

On the other hand, the drawback to cefaclor administration in suspension (sachets) is that, due to its saccharose content, its potential use is limited in diabetic patients, who must take the appropriate precautions.

Moreover, added to this drawback caused by the saccharose content, administration of cefaclor in suspension (phial) has further disadvantages which may be summarised as follows:

risk of accidental overdose due to uncontrolled consumption, particularly in children; and the difficulties of handling and transport because of the volume involved, leading to some risk of failure to complete the therapy, with the attendant loss of efficacy.

Retard tablets have the drawback of not permitting double dosage of the product; moreover, they are not suitable for patients with difficulties in ingesting solid forms.

Existing forms of administration of cefaclor do not in general meet entirely satisfactorily some requirements considered desirable in the treatment of bacterial infections, for example their application to any patient in conditions such as to ensure that the therapy is completed, thereby enhancing its efficacy.

There is thus a requirement for new pharmaceutical forms for administering cefaclor which solve these problems, making it easier for the patient to administer them, and so that they can be used with diabetic patients without causing additional difficulties, so increasing the efficacy of treatment. This invention provides a solution to these problems, by furnishing new pharmaceutical formulations containing cefaclor which are suitable for the manufacture of dispersible tablets.

Dispersible tablets are solid pharmaceutical forms for oral administration which must disintegrate in less than three minutes in water at 19° C.–21° C. and disperse evenly in the water. The dispersion uniformity trial involves placing two tablets in 100 ml of water and shaking them until they are completely disintegrated; they must disperse so as to pass through a screen with a nominal mesh size of 710 microns (*Brtitish Pharmacopea* Vol. II, 1988).

Dispersible tablets are known which contain antibiotics belonging to the synthetic penicillins group (amoxycillin) and anti-inflammatories (pyroxycam), but none is known which contains an antibiotic belonging to the synthetic cephalosporin group, such as cefaclor.

The subject of this invention is new pharmaceutical formulations containing cefaclor suitable for the manufacture of dispersible tablets. A further subject of this invention consists of such dispersible tablets containing cefaclor, and their manufacturing process.

A DETAILED DESCRIPTION OF THE INVENTION

The preparation of formulations suitable for manufacturing dispersible tablets requires both study of the physical-chemical incompatibilities of the active ingredient and a search for the right excipients making it possible to comply with the requirements of the various Pharmacopeas. Account must also be taken of the procedure to be used for the manufacture of such dispersible tablets, since the excipients and coadjuvants of the formulation will in large part depend on the process selected for the manufacture of such dispersible tablets. For reasons to be mentioned subsequently, direct compression was the process selected for the manufacture of the tablets.

The parameters defining dispersible tablets are as follows:

i) Their high rate of disintegration in water, and ii) The uniform distribution of the particles into which they disintegrate.

Disintegration rate and uniformity of dispersion are also dependent on both the coadjuvants and the active ingredient. Thus disintegration, as a measure of the release of the active ingredient in compressed pharmaceutical preparations, is the critical parameter for the development of dispersible forms. Thus the selection of coadjuvants in the preparation of dispersible tablets is the most important phase of the Galenic research. The properties and the quality of the finished tablet depend in large part on the coadjuvants it incorporates so that the correct choice of coadjuvant is of the greatest importance, as is the manufacturing process since the type of coadjuvant may be selected depending on the technique used.

New pharmaceutical formulations of cefaclor, suitable for manufacturing dispersible tablets provided by this invention, take account of these consideration and, in addition to the active ingredient, contain adequate amounts of disintegrator, diluents, lubricants, antiadherents, sweeteners, fragrances and, optionally, flavorings, flatting agents and colorings. In addition, in a particular implementation of this invention, new pharmaceutical formulations of cefaclor are provided which incorporate an effervescent pair.

Cefaclor is the active ingredient of the formulations in this invention. As used in this description, the term "cefaclor" is intended to include not only the free acid form but also its hydrates and pharmaceutically acceptable salts. The Cefaclor may be present in the formulation of an amount between 35% and 50% by weight of the total formulation weight. The cefaclor can be prepared as described for example in U.S. Pat. No. 3,925,372 and German Patent No. DE 2,408,698 (Eli Lilly & Co.).

Because the critical parameter of dispersible tablets is their rate of disintegration in water, the choice of the right disintegrator is one of the most important stages. As used in this description, the term "disintegrator" refers to an agent which produces a surface increase so that the active ingredient of the tablet is released very quickly. Glycolate sodium starch, alone or together with carboxymethylcellulose, polymeric derivates of acrylic acid and, preferably, crospovidone are suitable disintegrators for the formulations in this invention.

Glycolate sodium starch can be used in proportions of 5% and more by weight of the total formulation weight and, for preference, at concentrations between 10% and 21%. In addition, mixtures of glycolate sodium starch and sodium carboxymethylcellulose may be used in amounts of approximately 14% by weight of glycolate sodium starch and approximately 10% of sodium carboxymethylcellulose, in both cases in relation to the total weight of the formulation.

The polymeric derivative of acrylic acid may be of medium or high viscosity, preferably high, and may be used in a proportion of approximately 10% by weight of the total formulation weight.

The preferred disintegrator is a crospovidone (insoluble polyvinylpyrrolidone [PVP] obtained by polymerization of vinylpyrrolidone). This polymer can be included in the formulation in a proportion of approximately 10% by weight of the total formulation weight. It is believed that the high disintegrating action of the reticulated and insoluble PVP is due to its hydration capacity (water adsorption) which means that a very rapid tablet disintegration rate is attained with the resulting improved dissolution of the cefaclor in water.

On the other hand, the selection of the direct compression technique to manufacture dispersible tablets involves a further advantage in the choice of excipients. The possibility of using the disintegrator in extragranular form enhances its swelling effect since the disintegrating effect is not altered either by wetting or by drying.

In the sense used in this description, the term "diluents" includes excipients which facilitate the compression of powdery materials and give the tablets strength. Microcrystalline cellulose and dry flowing starch and mixtures thereof are suitable diluents.

The following are examples of suitable diluents for the formulations in this invention:

1) Microcrystalline cellulose, which provides the powder mixture with highly appropriate fluidity and compressibility characteristics. This diluent makes it possible to manufacture tablets of a high level of purity, using the direct compression technique. It also acts as a binder, to give strong tablets of suitable hardness, while its absorption capacity contributes to short disintegration times. Of the different types of microcrystalline cellulose available on the market, AVICEL PH102 (mean particle size 90 microns) is preferred; while the others have similar characteristics in terms of their capacity to facilitate direct compression, AVICEL PH102 makes direct compression more straightforward thanks to the fluidity it confers on the mixture and, because of its particle size, it facilitates direct compression of fine powder mixtures (as in the formulations of this invention). The microcrystalline cellulose may be present in the formulation at between 24% and 46% by weight of total formulation weight, and 2) dry flowing starch, due to its diluent and binding capacity in direct compression. It may be present in the formulation in a quantity of approximately 39% by weight of total formulation weight. However, tablets made with this diluent are not very hard, and this affects their friability negatively: for this reason, tablets containing microcrystalline cellulose as diluent are preferred.

Because of the very high percentage of microcrystalline cellulose (between 24% and 46% by weight of total formulation weight) tablets can be obtained with weights of between 1140 and 1150 mg, with high cellulose percentages, of the order of 38% to 46%, while with somewhat lower percentages—of the order of 35%–36%—tablets were obtained with a final weight of the order of 1125 mg each. Finally, when the percentage of microcrystalline cellulose is approximately 28%, tablets can be obtained with final weights of the order of 1130–1140 mg.

The term "lubricant" as used in this description includes excipients which reduce inter-particle friction inside the tablet, reducing the reaction forces appearing on the walls of the matrix. Stearyl sodium fumarate, a hydrophylic lubricant, may be used for preference as lubricant suitable for the formulations in this invention. This coadjuvant can be added to the formulations in this invention at a rate of less than 2% by weight in relation to the total weight of the formulation and, for preference, between 0.4% and 1.5% by weight of the total formulation weight.

The inclusion of this excipient enhances the slipping of the formulation to be compressed. It also ensures even filling of the space in the matrix so that there is very little tablet weight variation.

Standard stearic acid salts are not suitable since, for example, magnesium stearate does not adsorb water, giving a solution of most unpleasant appearance, with the formation of a "halo" on the surface.

The term "antiadherent" as used in this description includes excipients which prevent particle adhesion, so avoiding or reducing compacting and limiting friction between them. Colloidal silicon dioxide can be used as a suitable antiadherent for the formulations in this invention: because of its large specific surface, this raw material is a very good regulator of powder flow and also acts as adsorbent, capturing the humidity which would be taken up by the cefaclor, so slowing the degradation of the active ingredient by hydrolysis.

This coadjuvant can be incorporated at a percentage of less than 5% by weight of the total formulation weight and, for preference, between 0.2% and 1.5%.

The formulations in this invention may also contain sweeteners, fragrances and flavorings. Sodium saccharin may be used as artificial sweetener at less than 1% by weight of total weight of the formulation and, for preference, between 0.1% and 0.4% by weight, or aspartame at less than 1% by weight of total formulation weight and, for preference, between 0.2% and 0.75% by weight in relation to total weight of the formulation.

Strawberry fragrance may be used for preference as fragrance, for example that identified as 52,312 AP05.15 Firmenich, at between 3% and 6% by weight of the total formulation weight.

Anhydrous citric acid can be used for preference as flavoring, at between 2% and 4% by weight of total formulation weight.

Additionally and optionally, the formulations in this invention may contain a flatting agent and a colorant or combination of colorants to enhance the physical appearance of the solution to be obtained and to give it a uniform color. Titanium dioxide (E-171) may be used as an opacifier, in an amount less than 2% by weight of the total formulation weight, and for preference approximately 1.5% by weight of total formulation weight. Its use is not however essential.

Individual colorants or combinations may be used, preferably to obtain a red-pink solution which can be associated with the fragrance to be used in the tablets (strawberry) and which also provide the final suspension with a pleasant appearance. These objectives may be attained by including less than 1% by weight of the Red F, D and C No. 3—erythrosine (E-127) coloring [Merck Index, 11th Edition, 1989, Rahway, N.J., USA].

On the other hand, in a particular and alternative implementation of this invention, new pharmaceutical formulations of cefaclor are provided which also incorporate a pair of compounds which produce an effervescent effect. By including the effervescent pair, the tablet's disintegration rate can be increased. In general, an effervescent pair consists of an effervescent base, such as an alkaline or earth alkaline metal carbonate or bicarbonate and an acid which, on reacting with the effervescent base, produces carbon dioxide. In the new cefaclor formulations in this invention, any of the effervescent pairs normally used to make effervescent tablets can be employed, preferably that consisting of citric acid and calcium carbonate.

The cefaclor formulations obtained from this invention may be prepared easily by screening the appropriate amounts of the different excipients and coadjuvants and placing them in a suitable mixer. The active ingredient is then added and mixed until homogeneous, to give a free-flowing powder.

These new formulations can be used to make dispersible tablets containing cefaclor as active ingredient.

As already stated, the manufacturing process for the tablet plays a very important role in the design of the pharmaceutical formulation. The formation of the tablet casing may be based on a granulate (an agglomerated material made of powder particles to which a binder is added), or on a previously untreated powder mixture (direct compression). Coadjuvants are selected according to the technique selected. Because dispersible tablets are very sensitive to damp and their stability is compromised by granulation operations, direct compression is the preferred technique, being the one which offers most advantages: on the one hand, manufacture is rapid, depending neither on granulation or drying and, on the other, it avoids possible degradation (due to hydrolysis) of the active ingredient during granulation. Risk of contamination is also reduced. However, perhaps the most significant advantage is that directly compressed tablets normally disintegrate more rapidly than those made by wet granulation which require the addition of binding agents that slow the disintegration rate.

While direct compression may cause some drawbacks, such as problems of uniformity of mixture and dosage, fluidity and compressibility, surprisingly, with the formulations in this invention, none of these problems arose. In fact, the tablets varied very little in weight and content of active ingredient. Compressibility was acceptable and tablet hardness was within the required limits.

Dispersible tablets containing cefaclor may be manufactured by standard processes, for example in a conventional rotary or eccentric compressing machine which compresses the prepared and screened pharmaceutical formulation fed to the machine.

Dispersible tablets containing cefaclor provided by this invention are solid, intended for oral use, of uniform appearance, and with sufficient mechanical strength to withstand possible damage from storage and transport. The active ingredient is distributed evenly in the pharmaceutical form and the disintegration rate in water is high (within three minutes in water at 19° C.–21° C.). Likewise, the level of disintegration (or fineness of the particles in to which the product disintegrates) is suitable, and in line with the requirements of the various Pharmacopeas.

The use of dispersible tablets containing cefaclor provides a series of benefits over known and habitual forms of administration of this active ingredient, including the following:

They are suitable for treating patients with difficulties in ingesting solid forms;

They may be used by diabetic patients since they do not contain saccharose;

Dosage is flexible and reasonably accurate following dissolution in the volume of water desired by the patient.

The resulting solutions are of suitable organoleptic characteristics, acceptable to patients.

Their shape, size and reduced volume allow them to be presented in blister form, which is a benefit to the patient, enhancing ease of handling and carrying, to ensure that the patient completes the therapy, thereby raising the efficacy of treatment; and There is less risk of accidental intoxication due to overdose, making them less hazardous, particularly to children.

The following Examples illustrate specific implementations of the invention and should not be construed as limiting it. Said Examples use dry flowing starch [GORMASO], crospovidone (KOLLIDON CL®) [BASF] and microcrystalline cellulose (AVICEL PH 102®) [FMC FORET]. Both high- and medium-viscosity acrylic derivates consist of a copolymer of methacrylic acid and methyl methacrylate in a ratio of approximately 7:3, made by ROHM PHARMA. The difference between the two types of acrylic derivates is due to the different viscosity of the gel they form.

EXAMPLE 1

Dispersible tablets were prepared from the following pharmaceutical formulation:

| COMPONENTS | WEIGHT (mg) | % BY WEIGHT |
|---|---|---|
| Cefaclor | 523.01 | 37.35 |
| Glycolate sodium starch | 70.00 | 5.00 |
| CMC*, AVICEL PH102 | 612.99 | 43.78 |
| Stearyl sodium fumarate | 14.00 | 1.00 |
| Colloidal silicon dioxide | 70.00 | 5.00 |
| Aspartame | 10.00 | 0.71 |
| Strawberry fragrance | 50.00 | 3.58 |
| Anhydrous citric acid | 50.00 | 3.58 |

*CMC Microcrystalline cellulose

The process begins with the weighing of all the raw materials separately then screening them as a security measure. After screening, the excipients are placed in a suitable mixer, the cefaclor is then added and re-mixed until homogenous.

The mixed powders are passed several times through a 0.7 mm mesh screen. Compression follows, with periodic controls during the process, noting the results obtained on the associated control cards. The powder flows satisfactorily and compresses without difficulties. At the end of the process, representative samples are taken for analysis (from the beginning, middle and end of the batch) using a statistical sampling procedure.

Dispersible tablets were obtained with the following characteristics:

Individual tablet weight: 1400 mg±5%
Weight of 10 tablets: 14 g±3%
Hardness: 7 Kgf
Height: approximately 5.6 mm Diameter: 17.15 mm Disintegration in water at 19° C.–21° C.: <3 min Appearance: white with some transparent surface specks Flavor: pleasant (quite neutral)

Suspension: once disintegrated and shaken, remains in suspension approximately 2 minutes.

EXAMPLE 2

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 41.84 |
| Glycolate sodium starch | 62.50 | 5.00 |
| CMC*, AVICEL PH102 | 544.49 | 43.56 |
| Stearyl sodium fumarate | 12.50 | 1.00 |
| Colloidal silicon dioxide | 62.50 | 5.00 |
| Aspartame | 5.00 | 0.40 |
| Strawberry fragrance | 40.00 | 3.20 |

*CMC Microcrystalline cellulose

Dispersible tablets were obtained with the following characteristics:

Individual tablet weight: 1250 mg±5%

Weight of 10 tablets: 12.5 g±3%

Hardness: 7.8 Kgf

Height: approximately 5.5 mm

Diameter: 17.15 mm

Disintegration in water at 19° C.–21° C.: <3 min

Flavor: pleasant (quite neutral)

Suspension: once disintegrated and shaken, remains in suspension approximately 2 minutes.

EXAMPLE 3

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 41.84 |
| Glycolate sodium starch | 62.50 | 5.00 |
| CMC*, AVICEL PH102 | 574.49 | 45.96 |
| Stearyl sodium fumarate | 12.50 | 1.00 |
| Colloidal silicon dioxide | 12.50 | 1.00 |
| Sodium saccharin | 5.00 | 0.40 |
| Strawberry fragrance | 60.00 | 4.80 |

*CMC Microcrystalline cellulose

Dispersible tablets were obtained with the following characteristics:

Individual tablet weight: 1250 mg±5%

Weight of 10 tablets: 12.5 g±3%

Hardness: 8 Kgf

Height: approximately 5.2 mm

Diameter: 17.15 mm

Disintegration in water at 19° C.–21° C.: <3 min

Appearance: white-ish

Flavor: pleasant

Suspension: once disintegrated and shaken, remains in suspension approximately 2 minutes.

EXAMPLE 4

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.00 | 41.84 |
| Glycolate sodium starch | 62.50 | 5.00 |
| CMC*, AVICEL PH102 | 562.00 | 44.96 |
| Stearyl sodium fumarate | 12.50 | 1.00 |
| Colloidal silicon dioxide | 12.50 | 1.00 |
| Sodium saccharin | 5.00 | 0.40 |
| Strawberry fragrance | 60.00 | 4.80 |
| Titanium dioxide | 12.50 | 1.00 |

*CMC Microcrystalline cellulose

Dispersible tablets were obtained with the following characteristics:

Individual tablet weight: 1250 mg±5%

Weight of 10 tablets: 12.5 g±3%

Hardness: 10 Kgf

Height: approximately 5.1 mm

Diameter: 17.15 mm

Disintegration in water at 19° C.–21° C.: <3 min

Appearance: white-ish

Flavor: pleasant

Suspension: once disintegrated and shaken, appears to remain in suspension for a long period (approximately 30 minutes).

EXAMPLE 5

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 45.49 |
| Glycolate sodium starch | 115.00 | 10.00 |
| Dry flowing starch | 445.00 | 38.70 |
| Stearyl sodium fumarate | 6.25 | 0.54 |
| Colloidal silicon dioxide | 6.25 | 0.54 |
| Sodium saccharin | 3.00 | 0.27 |
| Strawberry fragrance | 45.00 | 3.92 |
| Titanium dioxide | 6.25 | 0.54 |

Dispersible tablets were obtained with the following characteristics:

Individual tablet weight: 1149.76 mg±5%

Weight of 10 tablets: 11.5 g±3%

Hardness: 8 Kp

Disintegration in water at 19° C.–21° C.: <3 min

Friability (10 tablets): 0.9%

Appearance: white-ish

Flavor: pleasant

Suspension: once disintegrated and shaken, appears to remain in suspension for a long period (approximately 30 minutes).

EXAMPLE 6

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 48.29 |
| Glycolate sodium starch | 163.00 | 15.05 |
| CMC*, AVICEL PH102 | 345.00 | 31.85 |
| Stearyl sodium fumarate | 5.60 | 0.52 |
| Colloidal silicon dioxide | 2.20 | 0.20 |
| Sodium saccharin | 3.00 | 0.28 |
| Strawberry fragrance | 38.00 | 3.51 |
| Titanium dioxide | 3.30 | 0.30 |

*CMC Microcrystalline cellulose

Dispersible tablets were obtained with the following characteristics:

Individual tablet weight: 1083.11 mg±5%

Weight of 10 tablets: 10.8 g±3%

Hardness: 8–9 Kgp

Disintegration in water at 19° C.–21° C.: <3 min

Friability (10 tablets): 0.8%

Appearance: white-ish

Flavor: pleasant

Suspension: once disintegrated and shaken, appears to remain in suspension for a long period (approximately 30 minutes).

EXAMPLE 7

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 45.88 |
| Glycolate sodium starch | 163.00 | 14.30 |
| Sodium carboxymethylcellulose | 120.00 | 10.53 |
| CMC*, AVICEL PH102 | 275.00 | 24.13 |
| Stearyl sodium fumarate | 5.60 | 0.49 |
| Colloidal silicon dioxide | 6.00 | 0.53 |
| Sodium saccharin | 2.00 | 0.17 |
| Strawberry fragrance | 42.00 | 3.68 |
| Titanium dioxide | 3.30 | 0.29 |

*CMC Microcrystalline cellulose

Dispersible tablets were obtained with the following characteristics:

Individual tablet weight: 1139.91 mg±5%

Weight of 10 tablets: 11.4 g±3%

Hardness: 8–9 Kp

Disintegration in water at 19° C.–21° C.: <3 min

Friability (10 tablets): 0.8%

Appearance: white-ish

Flavor: pleasant

Suspension: once disintegrated and shaken, appears to remain in suspension for a long period (approximately 30 minutes).

EXAMPLE 8

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 45.88 |
| Glycolate sodium starch | 110.01 | 9.65 |
| Calcium carbonate | 14.02 | 1.23 |
| Anhydrous citric acid | 40.01 | 3.51 |
| CMC*, AVICEL PH102 | 390.02 | 34.21 |
| Stearyl sodium fumarate | 5.59 | 0.50 |
| Colloidal silicon dioxide | 11.97 | 1.05 |
| Sodium saccharin | 2.05 | 0.18 |
| Strawberry fragrance | 40.01 | 3.50 |
| Titanium dioxide | 3.31 | 0.29 |

*CMC Microcrystalline cellulose

Dispersible tablets were obtained with the following characteristics:

Individual tablet weight: 1140 mg±5%

Weight of 10 tablets: 11.4 g±3%

Hardness: 9–10 Kp

Disintegration in water at 19° C.–21° C.: <3 min

Friability (10 tablets): 0.6%

Appearance: white-ish

Flavor: pleasant

EXAMPLE 9

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.10 |
| Glycolate sodium starch | 171.00 | 15.07 |
| CMC*, AVICEL PH102 | 345.00 | 31.35 |
| Stearyl sodium fumarate | 17.10 | 1.50 |
| Colloidal silicon dioxide | 17.10 | 1.50 |
| Sodium saccharin | 2.28 | 0.21 |
| Strawberry fragrance | 39.90 | 3.52 |
| Titanium dioxide | 8.55 | 0.75 |

*CMC Microcrystalline cellulose

Dispersible tablets were obtained with the following characteristics:

Individual tablet weight: 1134.62 mg±5%

Weight of 10 tablets: 11.3 g±3%

Hardness: 12.8 Kp

Disintegration in water at 19° C.–21° C.: <3 min

Friability (10 tablets): <0.5%

Appearance: white-ish

Flavor: pleasant

Suspension: once disintegrated and shaken, appears to remain in suspension for a long period (approximately 30 minutes).

EXAMPLE 10

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.10 |
| Glycolate sodium starch | 171.00 | 15.07 |

-continued

| COMPONENTS | WEIGHT (mg) | % BY WEIGHT |
|---|---|---|
| CMC*, AVICEL PH102 | 355.68 | 31.35 |
| Stearyl sodium fumarate | 17.10 | 1.50 |
| Colloidal silicon dioxide | 17.10 | 1.50 |
| Aspartame | 2.28 | 0.21 |
| Strawberry fragrance | 39.90 | 3.52 |
| Titanium dioxide | 8.55 | 0.75 |

*CMC Microcrystalline cellulose

Dispersible tablets were obtained with the following characteristics:

Individual tablet weight: 1134.62 mg±5%
Weight of 10 tablets: 11.3 g±3%
Hardness: 12.8 Kp
Disintegration in water at 19° C.–21° C.: <3 min
Friability (10 tablets): <0.5%
Appearance: white-ish
Flavor: pleasant
Suspension: once disintegrated and shaken, appears to remain in suspension for a long period (approximately 30 minutes).

EXAMPLE 11

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 45.96 |
| Glycolate sodium starch | 205.20 | 18.03 |
| CMC*, AVICEL PH102 | 324.90 | 28.55 |
| Stearyl sodium fumarate | 17.10 | 1.50 |
| Colloidal silicon dioxide | 17.10 | 1.50 |
| Sodium saccharin | 2.28 | 0.20 |
| Strawberry fragrance | 39.90 | 3.51 |
| Titanium dioxide | 8.55 | 0.75 |

*CMC Microcrystalline cellulose

Dispersible tablets were obtained with the following characteristics:

Individual tablet weight: 1138.04 mg±5%
Weight of 10 tablets: 11.4 g±3%
Hardness: 13.0 Kp
Disintegration in water at 19° C.–21° C.: <3 min
Friability (10 tablets): <0.5%
Appearance: white-ish
Flavor: pleasant
Suspension: once disintegrated and shaken, appears to remain in suspension for a long period (approximately 30 minutes).

EXAMPLE 12

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 45.96 |
| Glycolate sodium starch | 228.00 | 20.03 |
| CMC*, AVICEL PH102 | 302.10 | 26.55 |
| Stearyl sodium fumarate | 17.10 | 1.50 |
| Colloidal silicon dioxide | 17.10 | 1.50 |
| Sodium saccharin | 2.28 | 0.20 |
| Strawberry fragrance | 39.90 | 3.51 |
| Titanium dioxide | 8.55 | 0.75 |

*CMC Microcrystalline cellulose

Dispersible tablets were obtained with the following characteristics:

Individual tablet weight: 1138.04 mg±5%
Weight of 10 tablets: 11.4 g±3%
Hardness: 10.7 Kp
Disintegration in water at 19° C.–21° C.: <3 min
Friability (10 tablets): <0.5%
Appearance: white-ish
Flavor: pleasant
Suspension: once disintegrated and shaken, appears to remain in suspension for a long period (approximately 30 minutes).

EXAMPLE 13

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.66 |
| Acrylic derivate (medium viscosity) | 114.00 | 10.17 |
| CMC*, AVICEL PH102 | 399.00 | 35.60 |
| Stearyl sodium fumarate | 17.10 | 1.50 |
| Colloidal silicon dioxide | 17.10 | 1.50 |
| Sodium saccharin | 2.28 | 0.21 |
| Strawberry fragrance | 39.90 | 3.56 |
| Titanium dioxide | 8.55 | 0.76 |

*CMC Microcrystalline cellulose

Dispersible tablets were obtained with the following characteristics:

Individual tablet weight: 1120.94 mg±5%
Weight of 10 tablets: 11.2 g±3%
Hardness: 12.27 Kp
Disintegration in water at 19° C.–21° C.: <3 min
Friability (10 tablets): <0.5%
Appearance: white-ish
Flavor: pleasant
Suspension: once disintegrated and shaken, appears to remain in suspension for a long period (approximately 30 minutes).

EXAMPLE 14

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.26 |
| Acrylic derivate (high viscosity) | 114.00 | 10.08 |
| CMC*, AVICEL PH102 | 399.00 | 35.30 |
| Stearyl sodium fumarate | 17.10 | 1.51 |
| Colloidal silicon dioxide | 17.10 | 1.51 |
| Sodium saccharin | 3.42 | 0.30 |
| Strawberry fragrance | 39.90 | 3.53 |
| Titanium dioxide | 17.10 | 1.51 |

*CMC Microcrystalline cellulose

Dispersible tablets were obtained with the following characteristics:

Individual tablet weight: 1130.63 mg±5%

Weight of 10 tablets: 11.3 g±3%

Hardness: 13.65 Kp

Disintegration in water at 19° C.–21° C.: <3 min

Appearance: white-ish

Flavor: pleasant

Suspension: once disintegrated and shaken, appears to remain in suspension for a long period (approximately 30 minutes).

EXAMPLE 15

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.11 |
| Acrylic derivate (high viscosity) | 114.00 | 10.05 |
| CMC*, AVICEL PH102 | 399.00 | 35.17 |
| Stearyl sodium fumarate | 17.10 | 1.51 |
| Colloidal silicon dioxide | 17.10 | 1.51 |
| Sodium saccharin | 4.10 | 0.36 |
| Strawberry fragrance | 39.90 | 3.52 |
| Titanium dioxide | 17.10 | 1.51 |
| Erythrosine | 3.00 | 0.26 |

*CMC Microcrystalline cellulose

Dispersible tablets were obtained with the following characteristics:

Individual tablet weight: 1134.31 mg±5%

Weight of 10 tablets: 11.3 g±3%

Hardness: 13 Kp

Disintegration in water at 19° C.–21° C.: <3 min

Friability (10 tablets): <0.5%

Appearance: pale rose color

Flavor: pleasant

Suspension: once disintegrated and shaken, appears to remain in suspension for a long period (approximately 30 minutes).

EXAMPLE 16

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.24 |
| Acrylic derivate (high viscosity) | 114.00 | 10.08 |
| CMC*, AVICEL PH102 | 400.00 | 35.07 |
| Stearyl sodium fumarate | 17.10 | 1.51 |
| Colloidal silicon dioxide | 17.10 | 1.51 |
| Sodium saccharin | 4.10 | 0.36 |
| Strawberry fragrance | 40.00 | 3.53 |
| Yellow F, D and C No. 6 | 4.00 | 0.35 |
| Erythrosine | 4.00 | 0.35 |

*CMC Microcrystalline cellulose

Dispersible tablets were obtained with the following characteristics:

Individual tablet weight: 1131.31 mg±5%

Weight of 10 tablets: 11.3 g±3%

Hardness: 15.74 Kp

Disintegration in water at 19° C.–21° C.: <3 min

Friability (10 tablets): <0.5%

Appearance: pale rose color

Flavor: pleasant

Suspension: once disintegrated and shaken, appears to remain in suspension for a long period (approximately 30 minutes).

EXAMPLE 17

Dispersible tablets were prepared from the following pharmaceutical formulation, using the procedure described in Example 1:

| COMPONENTS | WEIGHT (mg) | % BY WEIGHT |
|---|---|---|
| Cefaclor | 523.01 | 46.48 |
| Acrylic derivate (high viscosity) | 114.00 | 10.13 |
| CMC*, AVICEL PH102 | 400.00 | 35.34 |
| Stearyl sodium fumarate | 17.10 | 1.52 |
| Colloidal silicon dioxide | 17.10 | 1.52 |
| Sodium saccharin | 4.10 | 0.36 |
| Strawberry fragrance | 40.00 | 3.56 |
| Erythrosine | 10.00 | 0.89 |

*CMC Microcrystalline cellulose

Dispersible tablets were obtained with the following characteristics:

Individual tablet weight: 1125.31 mg±5%

Weight of 10 tablets: 11.2 g±3%

Hardness: 15 Kp

Disintegration in water at 19° C.–21° C.: <3 min

Friability (10 tablets): <0.5%

Appearance: pale rose color

Flavor: pleasant

Suspension: once disintegrated and shaken, appears to remain in suspension for a long period (approximately 30 minutes).

EXAMPLE 18

Dispersible tablets were prepared from the following pharmaceutical formulation, using the procedure described in Example 1:

| COMPONENTS | WEIGHT (mg) | % BY WEIGHT |
| --- | --- | --- |
| Cefaclor | 523.01 | 46.48 |
| Crospovidone | 114.00 | 10.13 |
| CMC*, AVICEL PH102 | 400.00 | 35.34 |
| Stearyl sodium fumarate | 17.10 | 1.52 |
| Colloidal silicon dioxide | 17.10 | 1.52 |
| Sodium saccharin | 4.10 | 0.36 |
| Strawberry fragrance | 40.00 | 3.56 |
| Erythrosine | 10.00 | 0.89 |

*CMC Microcrystalline cellulose

Dispersible tablets were obtained with the following characteristics:

Individual tablet weight: 1125.31 mg±5%

Weight of 10 tablets: 11.2 g±3%

Hardness: 14.78 Kp

Disintegration in water at 19° C.–21° C.: <3 min

Friability (10 tablets): <0.5%

Appearance: pale rose color

Flavor: pleasant

Suspension: once disintegrated and shaken, appears to remain in suspension for a long period (approximately 30 minutes).

I claim:

1. A pharmaceutical formulation suitable for manufacturing dispersible tablets by direct compression, comprising (1) cefaclor as active ingredient in a quantity between 35% and 50% by weight of total formulation weight; (2) a disintegrator selected from the group consisting of glycolate sodium starch, acrylic derivatives, mixtures of glycolate sodium starch and carboxymethyl cellulose, and crospovidone; and (3) sodium stearyl fumarate, wherein the dispersible tablets disintegrate in water at 19°–21° C. and disperse evenly in the water in less than three minutes.

2. A formulation as set forth in claim 1, wherein the disintegrator is glycolate sodium starch in an amount between 5% and 21% by weight of total formulation weight.

3. A formulation as set forth in claim 1, wherein the disintegrator is an acrylic acid derivative in an amount of approximately 10% by weight of total formulation weight.

4. A formulation as set forth in claim 1, wherein the disintegrator is crospovidone in an amount of approximately 10% by weight of total formulation weight.

5. A formulation as set forth in claim 1, wherein the disintegrator is a mixture of (1) glycolate sodium starch in an amount of approximately 14% by weight of total formulation weight, and (ii) carboxymethylcellulose in an amount of approximately 10% by weight of total formulation weight.

6. A formulation as set forth in claim 1 comprising microcrystalline cellulose, dry flowing starch or a mixture thereof, as diluent.

7. A formulation as set forth in claim 6 comprising microcrystalline cellulose as diluent in an amount between 24% and 46% by weight of total formulation weight.

8. A formulation as set forth in claim 7 in which said microcrystalline cellulose has a mean particle size of approximately 90 microns.

9. A formulation as set forth in claim 6 comprising dry flowing starch as a diluent in an amount of approximately 39% by weight of total formulation weight.

10. A formulation as set forth in claim 1 which contains sodium stearyl fumarate in an amount of less than 2% by weight of total formulation weight.

11. A formulation as set forth in claim 1 comprising colloidal silicon dioxide as antiadherent, in an amount of less than 5% by weight of total formulation weight.

12. A formulation as set forth in claim 1 comprising a sweetener which is aspartame, sodium saccharin or a mixture thereof, in an amount of less than 1% by weight of total formulation weight.

13. A formulation as set forth in claim 12, wherein the sweetener is sodium saccharin in an amount between 0.1% and 0.4% by weight of total formulation weight.

14. A formulation as set forth in claim 12, wherein the sweetener is aspartame in an amount between 0.2% and 0.7% by weight of total formulation weight.

15. A formulation as set forth in claim 1 comprising a strawberry fragrance, in an amount between 3% and 5% by weight of total formulation weight.

16. A formulation as set forth in claim 1 comprising anhydrous citric acid as flavoring, in an amount between 2% and 4% by weight of total formulation weight.

17. A formulation as set forth in claim 1 comprising titanium dioxide as opacifier, in an amount of less than 2% by weight of total formulation weight.

18. A formulation as set forth in claim 1 comprising Red F, D and C No. 3—Erythrosine as colorant, in an amount of less than 1% by weight of total formulation weight.

19. A formulation as set forth in claim 1 which includes a pair of compounds capable of producing an effervescent effect on dispersion in water.

20. A formulation as set forth in claim 19, wherein said effervescent pair consists of citric acid and calcium carbonate.

21. A dispersible cefaclor tablet obtained by direct compression of the pharmaceutical formulation of claim 1.

22. A process for the manufacture of a dispersible tablet containing cefaclor, involving the direct compression of the pharmaceutical formulation of claim 1.

* * * * *